(12) United States Patent
Gast

(10) Patent No.: US 6,451,778 B1
(45) Date of Patent: Sep. 17, 2002

(54) ORAL CONTRACEPTIVE

(75) Inventor: Michael J. Gast, Phoenixville, PA (US)

(73) Assignee: Wyeth, Madison, NJ (US)

( * ) Notice: Subject to any disclaimer, the term of this patent is extended or adjusted under 35 U.S.C. 154(b) by 677 days.

(21) Appl. No.: 08/886,072

(22) Filed: Jul. 2, 1997

Related U.S. Application Data

(60) Provisional application No. 60/022,625, filed on Jul. 26, 1996.

(51) Int. Cl.$^7$ ................................................ A61K 31/56
(52) U.S. Cl. ....................................... 514/170; 514/843
(58) Field of Search ............................. 514/170, 843

(56) References Cited

U.S. PATENT DOCUMENTS

| | | |
|---|---|---|
| 3,957,982 A | 5/1976 | Lachnit-Fixson et al. |
| 3,969,502 A | 7/1976 | Lachnit-Fixson |
| 4,248,790 A | 2/1981 | Ponsold et al. |
| 4,273,771 A | 6/1981 | Coussediere |
| 4,390,531 A | 6/1983 | Edgren |
| 4,530,839 A | 7/1985 | Pasquale |
| 4,621,079 A | 11/1986 | Lachnit-Fixson et al. |
| 4,628,051 A | 12/1986 | Pasquale |
| 4,921,843 A | 5/1990 | Pasquale |
| 4,962,098 A | 10/1990 | Boissonneault |
| 5,262,408 A | 11/1993 | Bergink |
| 5,280,023 A | 1/1994 | Ehrlich et al. |
| 5,418,228 A | 5/1995 | Bennink |
| 5,547,948 A * | 8/1996 | Barcomb .................... 514/170 |
| 5,583,129 A | 12/1996 | Spona et al. |
| 5,633,242 A * | 5/1997 | Oettel et al. ................ 514/170 |

FOREIGN PATENT DOCUMENTS

| | | |
|---|---|---|
| DE | 4313926 | 11/1994 |
| EP | 0253607 | 1/1988 |
| EP | 0628312 | 12/1994 |
| EP | 0696454 | 2/1996 |
| WO | 9517194 | 6/1995 |
| WO | 9526730 | 10/1995 |

OTHER PUBLICATIONS

Sartoretto et al., Clinical evaluation of a low dosage estrogen–progesterone association (100μg of d–norgestrel and 20μg ethinyl [sic] estradiol), Clinica e Terapeutica (1974) 3:399–404.

* cited by examiner

*Primary Examiner*—Theodore J. Criares
(74) *Attorney, Agent, or Firm*—Arnold S. Milowsky

(57) ABSTRACT

This invention provides a method of contraception which comprises administering to a female of child beating age for a combination of a progestin at a daily dosage of 40–500 μg trimegestone, 250 μg–4 mg dienogest, or 250 μg–4 mg drospirenone, and an estrogen at a daily dosage equivalent in estrogenic activity to 10–20 μg ethinyl estradiol for 23–25 days beginning on day 1 of the menstrual cycle, and wherein the same dosage of the progestin and estrogen combination is administered in each of the 23–25 days.

24 Claims, No Drawings

ORAL CONTRACEPTIVE

This application claims the benefit of U.S. Provisional Application No. 60/022,625, filed Jul. 26, 1996.

BACKGROUND OF THE INVENTION

The vast majority of oral contraceptives consist of a combination of a progestin and estrogen that are administered concurrently for 21 days followed either by a 7 day pill free interval or by the administration of a placebo for 7 days in each 28 day cycle. The most important aspects of a successful oral contraceptive product are effective contraception, good cycle control (absence of spotting and breakthrough bleeding and occurrence of withdrawal bleeding), and minimal side effects. Combination oral contraceptives have traditionally acted by suppression of gonadotropins. In addition, it appears that the progestin component is primarily responsible for contraceptive efficacy through inhibition of ovulation, and other peripheral effects which include changes in the cervical mucus (which increase the difficulty of sperm entry into the uterus) and the endometrium (which reduce the likelihood of implantation). The estrogenic component intensifies the anovulatory effect of the progestin, and is also important for maintaining cycle control.

Since the introduction of oral contraceptives (OCs) over a quarter-century ago, research has been directed toward developing preparations that minimize the potential for side effects while maintaining efficacy and normal menstrual patterns. The first-generation OCs contained more progestin and estrogen than was necessary to prevent conception. Adverse hemostatic and metabolic changes, clinical problems, and side effects were associated with these high-dose preparations. In 1978, the World Health Organization (WHO) recommended that the focus of OC research should be the development of products containing the lowest possible dose levels of estrogen and progestin.

The first reductions in steroid content in a combination pill were focused on estrogen because it, rather than progestin, was thought to be related to the most serious side effects. Reduction in progestin content followed, as evidence mounted that lowering progestin intake might lower the risk of cardiovascular complications such as stroke and ischemic heart disease. [Kay CR, Am J Obstet Gynecol 142:762 (1982)]. However, this evidence was not as clear as that implicating estrogen in thromboembolic disorders. [Inman WHW, Br Med J 2:203 (1970); Stolley PD, Am J Epidemiol 102:197 (1975)]. The need for a balance between estrogens and progestins to minimize adverse effects on carbohydrate metabolism and on lipid and lipoprotein levels was also recognized. [Bradley D D, N Engl J Med 299:17 (1978); Wynn V, Lancet 1:1045 (1979)]. Researchers then found that the synergistic action between progestin and estrogen in a balanced ratio successfully inhibited ovulation at low levels of both components.

Research into low-dose progestins was advanced significantly by the development of norgestrel (Ng) and levonorgestrel (LNg). Levonorgestrel is the biologically active moiety of racemic norgestrel. It is strongly progestational, has no inherent estrogenic activity, is antiestrogenic, and possesses good biologic activity. The contraceptive effects of levonorgestrel are manifested throughout the hypothalamic-pituitary-gonadal-target organ axis.

Ethinyl estradiol (EE) is the estrogen most frequently used in combination OCs. In attempts to fulfill the WHO objective, the dosage of EE in marketed OC formulations has been steadily reduced from that found in earlier OCs. Thromboembolic mortality decreased when the amount of synthetic estrogen in OC formulations was reduced from 100 $\mu$g to 50 $\mu$g. Subsequently, a significant reduction in fatal myocardial infarctions was reported for women using OCs with 30 $\mu$g of EE rather than 50 $\mu$g of EE. [Meade TW, Br Med J 280:1157 (1980)].

In keeping with the goal of reducing the total steroidal dosage, while maintaining contraceptive efficacy, good cycle control, and minimizing side effects, numerous regimens have been developed in which the progestin/estrogen combination is administered either as a fixed dosage combination (monophasic) or as biphasic or triphasic regimens in which the dosage of the combination is varied either once or twice throughout the menstrual cycle. In these regimens, the progestin/estrogen combination is typically administered for 21 days followed by either a 7-day pill free period or the administration of a non-contraceptive placebo (or iron supplement) for 7 days. In these regimens, 3-ketodesogestrel (3-KDSG), desogestrel (DSG), levonorgestrel (LNg), gestodene (GTD), norgestrel (NG), and norethindrone (NE) are typically used as the progestin while ethinyl estradiol (EE); 17$\beta$-estradiol, and mestranol are typically the estrogenic components. Other progestins less frequently used include drospirenone (DRSP) and dienogest (DGST).

An oral contraceptive product containing a combination of 3 mg DGST and 30 $\mu$g EE for 21-day administration per cycle is marketed in Germany.

Several examples of attempts at reducing the total steroidal dosage are provided below.

Spona (PCT Publication WO 95/17194) discloses contraceptive regimens which consist of the administration of a combinaton of a progestin (50–75 $\mu$g GTD, 75–125 $\mu$g LNg, 60–150 $\mu$g DSG, 60–150 $\mu$g 3-KDSG, 100–300 $\mu$g DRSP, 100–200 $\mu$g cyproterone acetate, 200–300 $\mu$g norgestimate, or >350–750 $\mu$g norethisterone) and an estrogen (15–20 $\mu$g EE or 2–6 mg 17$\beta$-estradiol) for 23–24 days per cycle.

Oettel (EP 628,312 A1) discloses combination contraceptive combinations containing the combination of three components: a biogenic estrogen (estradiol, estrone, or estriol), a synthetic estrogen (EE or mestranol), and a progestin (LNg, desogestrel, progesterone, norethisterone acetate, DGST, chlormadinone acetate, gestodene, or cyproterone acetate). In one embodiment, the combination is administered for 21 days followed by the administration of placebo (or pill free) or an estrogen on days 22–28 of the cycle.

Oettel (EP 696,454 A2) discloses a three phase contraceptive regimen in which the first phase consists of the administration for 3–4 days of a composition containing at least one biogenic estrogen; the second phase consists of the administration for 20–22 days of at least one biogenic estrogen and at least one progestin (progesterone, DGST, desogestrel, 3-KDSG, GTD, LNg, norgestimate, notethisterone, norethisterone acetate, dehydrogestrone, chloromadinone acetate, cyproterone acetate, medroxyprogesterone acetate, or megestrol acetate); and the third phase consists of the administration for 3–4 days of a composition containing at least biogenic one estrogen.

Lachnit (PCT Publication WO 95/26730) discloses bridged regimens consisting of the administration of a combination of a progestinlestrogen combination (50–125 $\mu$g LNg and 10–40 $\mu$g EE) for the first 23–24 days of the menstrual cycle followed by the administration of an estrogen (2–40 $\mu$g EE) for 4–10 days for a total administration of at least 28 days per cycle. The use of 100–300 $\mu$g drospirenone and 10–40 $\mu$g EE as the 23–24 day progestin/ estrogen combination is disclosed. Lachnit also discloses a triphasic plus bridging regimen (4–9 days, 4–9 days, 9–13 days, and 28 days for the three phases and estrogen phase, respectively) in which a combination of 50 µg LNg and 20 µg EE are administered in the first phase, a combination of 75 µg LNg and 25 µg EE are administered in the second phase, a combination of 100 µg LNg and 20 µg EE are administered in the third phase, and 10 µg EE is administered in the estrogen phase. Other progestins disclosed include GTD, DSG, 3-KDSG, DRSP, cyproterone acetate, norgestimate, and norethisterone.

Upton (EP Patent Specification 253,607 B 1) teaches the use of low dose progestin/estrogen combinations for combined hormone replacement therapy and contraception in climacteric women. Climacteric women are defined in Upton as pre-menopausal women around 40 years of age whose hormone levels are waning. The climacteric woman still ovulates (albeit may have irregular ovulation), but she still experiences many of the symptoms of the hypoestrogenic menopausal woman, such as insomnia, hot flushes, and irritability. Upton teaches the administration of a 23–26 day monophasic regimen of progestin/estrogen followed by a pill free or placebo interval of 2–5 days; with 24 days of progestin/estrogen administration followed by a 4-day pill free or placebo administration being preferred. Upton teaches the use of a progestin selected from 25–100 LNg, 10–70 µg GTD, 25–100 g DSG, 25–100 g 3-KDSG, and 85–350 µg NE used in combination with an estrogen selected from 500–2000 µg 17β-estradiol, 8–30 µg EE, and 15–60 µg mestranol. Based on relative potencies, Upton teaches that a dose of 75 µg LNg is equivalent to 35 µg of GTD, 75 µg of 3-KDSG or DSG, and 250 µg NE and that a dose of 1000 µg of 17β-estradiol is equivalent to a dose of 15 βg EE and 30 µg mestranol. Upton also teaches that NG may be substituted for LNg, but at twice the dose.

Saitoretto (Clinica e Terapeutica 3: 399 (1974)) discloses a monophasic contraceptive regimen consisting of the administration of a combination 100 µg LNg and 20 µg EE for 21 days.

Lachnit-Fixson (U.S. Pat. No. 3,969,502) discloses biphasic progestin/estrogen combination regimens in which a combination of 50–125 µg LNg. and 25–35 µg EE are administered for 10–12 days in the first phase and 100–350 µg LNg and 30–50 µg EE are administered for 10–12 days in the second phase. Placebo is administered for 5–7 days following the administration of the contraceptive steroid regimen.

Lachnit-Fixson (U.S. Pat. No. 3,957,982) discloses triphasic 21-day progestin/estrogen regimens in which a combination of 40–90 µg LNg and 20–50 µg EE is administered for 4–6 days in the first phase, 50–125 µg LNg and 30–50 µg EE is administered for 4–6 days in the second phase, and 100–250 µg LNg and 25–50 µg EE is administered for 9–11 days in the third phase. It is preferred that the first, second, and third phases are 6, 5, and 10 days, respectively.

Bennick (U.S. Pat. No, 5,418,228) discloses triphasic regimens which consist of the administration of a combination progestinlestrogen in a 6–8 day phase, a second 6–8 day phase, and a third 6–8 day phase, with it being preferred that the three contraceptive steroid phases be 7 days each. Bennick discloses that the first contraceptive steroid phase consists of a progestin at a daily dosage equivalent to 75–150 µg DSG and an estrogen at a daily dosage equivalent to 20–25 µg EE; the second contraceptive steroid phase consists of a progestin at a daily dosage equivalent to 75–125 µg DSG and an estrogen at a daily dosage equivalent to 20 µg EE; and the third contraceptive steroid phase consists of a progestin at a daily dosage equivalent to 75–100 µg DSG and an estrogen at a daily dosage equivalent to 20 µg EE. Placebo is administered for 7 days following the 21-day contraceptive steroid period. Bennick discloses that the progestin may be 3-KDSG, DSG, LNg, or GTD.

Bergink (U.S. Pat. No. 5,262,408) discloses a 24 day triphasic combination regimen in which the first 7–9 day phase consists of the administration of a progestin at a daily dosage equivalent to 100 µg DSG and an estrogen at a daily dosage equivalent to 25 µg EE, the second 7–9 day phase consists of the administration of a progestin at a daily dosage equivalent to 125 µg DSG and an estrogen at a daily dosage equivalent to 20 µg EE, and the third 7–9 day phase consists of the administration of a progestin at a daily dosage equivalent to 50 µg DSG and an estrogen at a daily dosage equivalent to 20 µg EE. It is preferred that the three phases be 8 days each. Following the 24 day contraceptive steroid administration, a placebo may be administered for 4 days, the 4 day interval may be pill free, or a progestin at a dosage equivalent to 25–35; µg DSG may be administered.

Boissonneault (U.S. Pat. No. 4,962,098) discloses triphasic progestinlestrogen combinations in which the amount of the estrogenic component is increased stepwise over the three phases. Contraceptive steroid combinations are taken for 4–7 days during the first phase (5 days being preferred); for 5–8 days during the second phase (7 days preferred); and for 7–12 days during the third phase (9 days being preferred). Following the administration of 21-days of the contraceptive steroid combination, placebo is taken for 7 days. For all three phases, 0.5–1.5 mg of norethindrone acetate is used in the progestin, with 1 mg being preferred. 10–30 µg EE is used in the first phase, 20–40 µg in the second, and 30–50 µg in the third phase.

Pasquale (U.S. Pat. No. 4,921,843) discloses combination progestin/estrogen contraceptive regimens which contain 0.5 to 1 mg of progestin and an estrogen having a dose equivalent to 10–40 µg of EE. NE, LNg, D-17β-acetoxy-13β-ethyl-17α-ethinyl-gon-4-en-3-one oxime, and 19-nor-17-hydroxy progesterone ester are disclosed as progestins, with NE being preferred. Specifically disclosed regimens include a uniphasic regimen (2 days of placebo, 5 days of 20 µg EE, and 21 days of a combination of 500 µg NE and 35 µg EE); a uniphasic regimen (2 days of placebo, 5 days of 40 µg EE, and 21 days of a combination of 500 µg NE and 35 µg EE); and a triphasic regimen (2 days of placebo; 5 days of 20–40 µg EE; 7 days of a combination of 500 µg NE and 35 µg EE; 7 days of a combination of 750 µg NE and 35 µg EE; and 7 days of a combination of 1 mg NE and 35 µg EE).

Pasquale (U.S. Pat. No. 4,628,051) discloses triphasic progestin/estrogen combination regimens in which contraceptive steroid is administered for 21 days. Contraceptive steroid combinations are taken for 5–8 days during the first phase (7 days being preferred); for 7–11 days during the second phase (7 days preferred); and for 3–7 days during the third phase (7 days being preferred). In all three phases, an estrogen at a daily dosage equivalent to 20–50 µg EE is administered in combination with a progestin having a daily dosage equivalent to 65–750 µg NE in the first phase, 0.25–1.0 mg NE in the second phase, and 0.35–2.0 mg NE in the third phase. A specific triphasic regimen discloses the administration of 35 µg EE in each of the three 7-day phases in combination with 0.5 mg, 0.75 mg, and 1.0 mg in the first, second, and third phases, respectively. A second specific triphasic regimen discloses the administration of 35 µg EE in each of the three 7-day phases in combination with 50 μg, 75 μg, and 100 μg in the first, second, and third phases, respectively. A third specific triphasic regimen discloses the administration of 35 μg EE in each of the three 7-day phases in combination with 25 μg, 35 μg, and 50 μg in the first, second, and third phases, respectively.

Lachnit-Fixson (U.S. Pat. No. 4,621,079) discloses triphasic 21-day progestin/estrogen combination regimens in which a combination of 40–70 μg GTD and 20–35 μg EE is administered for 4–6 days in the first phase; 50–100, μg GTD and 30–50 μg EE is administered for 4–6 days in the second phase; and 80–120 μg GTD and 20–50 μg EE is administered for 9–11 days in the third phase. Placebo is administered for 7 days following the 21-day contraceptive steroid regimen.

Pasquale (U.S. Pat. No. 4,530,839) discloses triphasic 21-day progestin/estrogen combination regimens in which a dose of 20–50 μg EE is administered in all three phases in combination with a contraceptively effective daily dose of progestin in the first phase, 1.5–2 times that dose of progestin in the second phase, and 2–2.5 times the first phase dose of progestin in the third phase. Each of the three phases is 7 days long. A specific regimen discloses 20–50 μg EE in combination with 500 μg LNg, 750 μg LNg, and 1 mg LNg during each of the three 7-day phases, respectively.

Edgren (U.S. Pat. No. 4,390,531) discloses triphasic 21-day progestin/estrogen combination regimens in which a dose of 20–40 μg EE (or another estrogen in an equivalent dosage) is administered in all three phases in combination with 0.3–0.8 mg NE (or another progestin in an equivalent dosage) for 5–8 days in the first phase, twice the dose of NE for 7–11 days in the second phase, and the dose of NE being the same as in the first phase for 3–7 days in the third phase. It is preferred that each of the three phases is 7 days. Placebo is administered for 6–8 days following administration of the contraceptive steroid combination. A specific regimen discloses a first phase of 7 days of 0.5 mg NE in combination with 35 μg EE, a second 7 day phase of 1.0 mg NE in combination with 35 μg EE, and a third 7 day phase of 0.5 mg NE in combination with 35 μg EE.

Moore (DE 4313926 Al) discloses bridged triphasic regimens consisting of the administration of a combination of 10–50 μg LNg and 5–20 μg EE from days 1–7 of the menstrual cycle; of 50–75 μg LNg and 5–20 μg EE from days 8–14 of the menstrual cycle; of 75–125 μg LNg and 5–20 μg EE from days 15–21 of the menstrual cycle; and 5–20 μg EE from days 22–28 of the menstrual cycle.

Erlich (German Patent DE 4,104,385 C1 and U.S. Pat. No. 5,280,023) discloses sequential contraceptive regimens consisting of the administration of an estrogen which effects a disturbance of follicle stimulation, followed by the administration of a combination of a progestin/estrogen in a dose at least adequate to inhibit ovulation. The regimen is administered for a total of 28 days per cycle. It is preferred that the estrogen is administered for 5–14 days per cycle and the progestin/estrogen combination is administered for 23–14 days per cycle, so that the total administration is for 28 days per cycle. Specific regimens include (a) 4 mg estradiol for 7 days followed by 21 days of the combination of 1 mg norethisterone acetate and 4 mg estradiol; (b) 2 mg estradiol valerate for 7 days followed by 21 days of the combination of 2 mg chlormadinone acetate and 4 mg estradiol valerate; and (c) 20 μg EE followed by 18 days of the combination of 150 μg LNg and 20 μg EE. Regimen (c) in Erlich provides a total steroidal load of 2.7 mg of LNg and 560 μg EE per 28 day cycle.

DESCRIPTION OF THE INVENTION

This invention provides a monophasic combination progestin/estrogen oral contraceptive regimen for females of child-bearing age that provides effective contraception, good cycle control, and minimal side effects while greatly reducing the total contraceptive steroid administered (particularly the estrogenic component) per 28-day cycle. To achieve the substantial reduction in the total contraceptive steroid administered per cycle while maintaining good cycle control, the low dose progestin/estrogen combination is administered for 23–25 days per cycle. Administration of the contraceptive progestin/estrogen combination is begun on the first day of menses (day 1), and continued for 23–25 consecutive days. Following the 23–25-day administration period, a non-contraceptive placebo (devoid of progestins and estrogens) can be provided for 3–5 days to aid in compliance with the desired contraceptive regimen. Alternatively, the 3–5-day interval can be pill free. The total cycle length is 28 days.

More particularly, this invention provides a method of contraception which comprises administering to a female of child bearing age a combination of 40–500 μg trimegestone, 250 μg–4 mg dienogest, or 250 μg–4 mg drospirenone, and an estrogen at a daily dosage equivalent in estrogenic activity to 10–20 μg ethinyl estradiol for 23–25 days beginning on day 1 of the menstrual cycle. Following the 23–25-day administration period, a non-contraceptive placebo (devoid of progestins and estrogens) can be provided for 3–5 days to aid in compliance with the desired contraceptive regimen. Alternatively, the 3–5-day interval can be pill free. The total cycle length is 28 days.

Preferred estrogens include, but are not limited to ethinyl estradiol; 17β-estradiol; conjugated estrogens, USP; estrone or a salt thereof; and mestranol; with ethinyl estradiol being more preferred. When ethinyl estradiol is used as the estrogen, it is preferred that the daily dosage of ethinyl estradiol is 10–20 μg, with 15 μg being more preferred. Preferred salts of estrone include, but are not limited to the sodium and piperate salt. When conjugated estrogens, USP are used as the estrogen, it is preferred that the daily dosage is 0.3–5 mg, with a daily dose of 1.25 mg conjugated estrogens, USP being equivalent to a daily dose of 15 μg ethinyl estradiol.

Following the 23–25-day period, a non-contraceptive placebo, which may contain an iron supplement, such as 75 mg of ferrous fumarate, may be administered for 4 days (through day 28 of the menstrual cycle) or the 4 days following administration of the contraceptive combination may be pill free.

It is preferred that the progestin/estrogen combination be administered for 24 days beginning on day 1 of the menstrual cycle.

The following daily dosages of a combination of trimegestone and ethinyl estradiol are preferred for contraception when administered for 23–25 consecutive days beginning on the first day of menses. Regimen B is most preferred.

| PREFERRED DAILY DOSAGES | | |
|---|---|---|
| Regimen | Trimegestone | Ethinyl Estradiol |
| A | 250 μg | 15 μg |
| B | 125 μg | 15 μg |
| C | 75 μg | 15 μg |

-continued

PREFERRED DAILY DOSAGES

| Regimen | Trimegestone | Ethinyl Estradiol |
|---------|--------------|-------------------|
| D | 50 µg | 15 µg |
| E | 40 µg | 15 µg |

The following daily dosages of a combination of dienogest and ethinyl estradiol are preferred for contraception when administered for 23–25 consecutive days beginning on the first day of menses. Regimen B is most preferred.

PREPERRED DAILY DOSAGES

| Regimen | Dienogest | Ethinyl Estradiol |
|---------|-----------|-------------------|
| A | 2 mg | 15 µg |
| B | 1 mg | 15 µg |
| C | 800 µg | 15 µg |
| D | 750 µg | 15 µg |
| E | 500 µg | 15 µg |

The following daily dosages of a combination of drospirenone and ethinyl estradiol are preferred for contraception when administered for 23–25 consecutive days beginning on the first day of menses. Regimen C is most preferred.

PREFERRED DAILY DOSAGES

| Regimen | Drospirenone | Ethinyl Estradiol |
|---------|--------------|-------------------|
| A | 3 mg | 15 µg |
| B | 2 mg | 15 µg |
| C | 1 mg | 15 µg |
| D | 500 µg | 15 µg |

It is preferred that the combination progestin/estrogen contraceptive be administered in unit dosage form i.e., tablet or pill, with each unit providing the entire daily dosage. It is preferred that the progestin and estrogen are admixed together in the same dosage unit. Such dosage units can be prepared by conventional methodology that is well known to one skilled in the art. In each dosage unit, the contraceptively active progestin and estrogen are combined with excipients, vehicles, pharmaceutically acceptable carriers, and colorants. For example, the following illustrates an acceptable composition of a contraceptive progestin/estrogen combination of this invention.

EXAMPLE 1

Trimegestone, 125 µg
Ethinyl estradiol, 15 µg
Microcrystaline Cellulose
Lactose, NF, Spray Dried
Polacrillin Potassium, NF
Magnesium Stearate
Opadry Pink
Polyethylene Glycol, 1500, Flakes
Water, Purified, USP
Wax E (Pharma)

This invention also provides a contraceptive kit adapted for daily oral administration which comprises 23–25 separate dosage units, said dosage units each consisting of a combination of 40–500 µg trimegestone, 250 µg–4 mg dienogest, or 250 µg–4 mg mg drospirenone, and an estrogen at a daily dosage equivalent in estrogenic activity to 10–20 µg ethinyl estradiol In another embodiment, the contraceptive kit contains 28 daily dosage units with 3–5 being a non-contraceptive placebo, that may contain an iron supplement, such as 75 mg ferrous fumarate. The daily dosage arrangements are preferably arranged in a blister pack or in a dial pack type tablet dispenser.

What is claimed is:

1. A method of contraception which comprises administering to a female of child bearing age a combination of a progestin at a daily dosage selected from the group consisting of 40–500 µg trimegestone, and 250 µg–4 mg dienogest, and an estrogen at a daily dosage equivalent in estrogenic activity to 10–20 µg ethinyl estradiol for 23–25 days beginning on day 1 of the menstrual cycle, and wherein the same dosage of the progestin and estrogen combination is administered in each of the 23–25 days.

2. The method according to claim 1, wherein the estrogen is selected from the group consisting of ethinyl estradiol; 17β-estradiol; conjugated estrogens, USP; estrone or a salt thereof; and mestranol.

3. The method according to claim 2, wherein the estrogen is ethinyl estradiol.

4. The method according to claim 3, wherein the progestin/estrogen combination is administered for 24 days per menstrual cycle beginning on day 1 of the menstrual cycle.

5. The method according to claim 4 wherein the daily dosage of ethinyl estradiol is 15 µg.

6. The method according to claim 5, wherein the progestin is trinegestone.

7. The method according to claim 6, wherein the daily dosage of trimegestone is 250 µg.

8. The method according to claim 6, wherein the daily dosage of trimegestone is 125 µg.

9. The method according to claim 6, wherein the daily dosage of trimegestone is 75 µg.

10. The method according to claim 6, wherein the daily dosage of trimegestone is 50 µg.

11. The method according to claim 6, wherein the daily dosage of trimegestone is 40 µg.

12. The method according to claim 5, wherein the progestin is dienogest.

13. The method according to claim 11, wherein the daily dosage of dienogest is 2 mg.

14. The method according to claim 11, wherein the daily dosage of dienogest is 1 mg.

15. The method according to claim 11, wherein the daily dosage of dienogest is 800 µg.

16. The method according to claim 11, wherein the daily dosage of dienogest is 750 µg.

17. The method according to claim 11, wherein the daily dosage of dienogest is 500 µg.

18. The method according to claim 1, which further comprises administering a non-contraceptive placebo for 3–5 consecutive days beginning on the day immediately following the last day of administration of the progestin/estrogen combination, such that the total days of administration of the progestin/estrogen combination plus the non-contraceptive placebo equals 28 days.

19. The method according to claim 18 in which the non-contraceptive placebo contains an iron supplement.

20. A contraceptive kit adapted for oral administration consisting of 23–25 separate dosage units, said dosage units each containing a combination of a progestin at a dosage selected from the group consisting of 40–500 µg trimegestone, and 250 µg–4 mg dienogest, and an estrogen at a dosage equivalent in estrogenic activity to 10–20 µg ethinyl estradiol, wherein each of the dosage units contains the same dosage of progestin and estrogen.

21. The contraceptive kit according to claim 20, wherein the estrogen is selected from the group consisting of ethinyl estradiol; 17β-estradiol; conjugated estrogens, USP; estrone or a salt thereof; and mestranol.

22. The contraceptive kit according to claim 21, wherein the estrogen is ethinyl estradiol.

23. The contraceptive kit according to claim 22 in which the number of dosage units is 24.

24. A contraceptive kit adapted for oral administration which comprises 28 dosage separate units, 23–25 of said dosage units each containing a combination of a progestin at a dosage selected from the group consisting of 40–500 µg trimegestone, and 250 4g–4 mg dienogest, and an estrogen at a dosage equivalent in estrogenic activity to 10–20 µg ethinyl estradiol, wherein each of the dosage units contains the same dosage of progestin and estrogen; and 3–5 of said dosage units each containing a non-contraceptive placebo; wherein each of the 23–25 dosage units contains the same dosage of progestin and estrogen.

* * * * *